(12) United States Patent
Bonifacio et al.

(10) Patent No.: US 7,189,876 B2
(45) Date of Patent: Mar. 13, 2007

(54) METHODS FOR PREPARING SERTRALINE HYDROCHLORIDE POLYMORPHS

(75) Inventors: Fausto Bonifacio, Latina (IT); Cristina Crescenzi, Rome (IT); Maria Donnarumma, Latina (IT); Dimitri Ippoliti, Aprilia (IT)

(73) Assignee: Recordati Industria Chimica e Farmaceutica S.p.A., Milan (IT)

( * ) Notice: Subject to any disclaimer, the term of this patent is extended or adjusted under 35 U.S.C. 154(b) by 193 days.

(21) Appl. No.: 10/891,441

(22) Filed: Jul. 14, 2004

(65) Prior Publication Data
US 2005/0032907 A1 Feb. 10, 2005

Related U.S. Application Data

(60) Provisional application No. 60/487,505, filed on Jul. 15, 2003.

(51) Int. Cl.
| | |
|---|---|
| *C07C 209/82* | (2006.01) |
| *C07C 209/84* | (2006.01) |
| *C07C 209/86* | (2006.01) |
| *C07C 211/35* | (2006.01) |

(52) U.S. Cl. .................... 564/308; 564/424; 564/428

(58) Field of Classification Search ............... None
See application file for complete search history.

(56) References Cited

U.S. PATENT DOCUMENTS

| 4,536,518 A | 8/1985 | Welch, Jr. et al. |
| 5,248,699 A | 9/1993 | Sysko et al. |
| 6,495,721 B1 | 12/2002 | Schwartz et al. |
| 6,500,987 B1 | 12/2002 | Schwartz et al. |
| 6,897,340 B2 | 5/2005 | Schwartz et al. |

FOREIGN PATENT DOCUMENTS

WO  WO0190049  11/2001

OTHER PUBLICATIONS

International Search Report completed on Oct. 26, 2004 and issued to a related foreign application. (PCT/EP2004/051489).

*Primary Examiner*—Brian Davis
(74) *Attorney, Agent, or Firm*—Ohlandt, Greeley, Ruggiero & Perle, L.L.P.

(57) ABSTRACT

This invention relates to crystalline polymorphs of sertraline hydrocloride, i.e. (1S-cis)-4-(3,4-dichlorophenyl)-1,2,3,4-tetrahydro-N-methyl-1-naphtalenamine hydrochloride, denominated form I, II and V, and methods for their preparation.

18 Claims, No Drawings

METHODS FOR PREPARING SERTRALINE HYDROCHLORIDE POLYMORPHS

RELATED APPLICATIONS

This application claims priority to U.S. Provisional application No. 60/487,505 filed Jul. 15, 2003 which is incorporated herein by reference in its entirety.

BACKGROUND OF THE INVENTION

Sertraline hydrochloride is a known compound having the following structural formula:

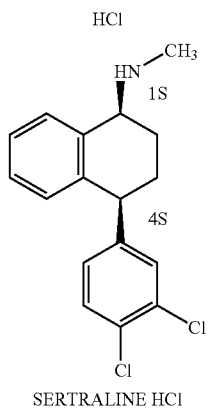

SERTRALINE HCl

Sertraline, in the form of its hydrochloride salt, is the active principle of the medicinal product known under the trademark Zoloft®, useful in the treatment of depression, obsessive-compulsive disorders, panic disorders and premature ejaculation.

Sertraline hydrochloride can exist in different crystalline forms which differ from each other in terms of stability, physical properties, spectral data and methods of preparation.

U.S. Pat. No. 4,536,518 (Pfizer Inc.) describes a synthesis of sertraline hydrochloride by treating an ethyl acetate/ether solution of free base with gaseous hydrogen chloride. This patent does not refer to specific polymorphic crystalline forms of sertraline hydrochloride.

U.S. Pat. No. 5,248,699 (Pfizer Inc.) discloses 5 polymorphic forms of sertraline hydrochloride (I, II, III, IV and V), which can be characterized by single crystal x-ray analysis, powder x-ray diffraction, infra-red spectroscopy and differential scanning calorimetry.

According to U.S. Pat. No. 5,248,699, sertraline hydrochloride produced by the method of U.S. Pat. No. 4,536,518 has a crystalline form corresponding to form II.

U.S. Pat. No. 5,734,083 (Torcan Chemical Ltd.) discloses another polymorphic form of sertraline hydrochloride (=T 1), and the process of preparation thereof.

U.S. Pat. No. 6,500,987 (Teva Pharm. Ind.) describes processes for making sertraline hydrochloride form II, III IV and V and mentions further crystalline forms of sertraline hydrochloride, such as form VI (solvated crystal form with methanol or ethanol), forms VII–IX (different hydrate forms) and form X (solvated crystal form with benzyl alcohol)

Sertraline hydrochloride is usually prepared by acidification of a solution of sertraline base or a salt thereof with hydrogen chloride (both gaseous hydrogen chloride and aqueous hydrogen chloride).

The preparation of sertraline hydrochloride by addition of aqueous hydrochloric acid is a straight process but it is characterized by lower yields due to solubility of sertraline hydrochloride in water.

The alternative use of gaseous hydrogen chloride on a large scale would give rise to high equipment costs and typical risks of gas handling.

DESCRIPTION OF THE INVENTION

The present invention relates to a new method for preparing sertraline hydrochloride form I, II or V in which a solution of sertraline base or a salt thereof in a suitable solvent is reacted with an amine hydrochloride, and sertraline hydrochloride precipitates in a crystallized form and is separated by filtration, preferably as a selected crystalline form according to said solvent.

According to the purposes of the invention, an amine hydrochloride has shown to represent a highly convenient source of hydrogen chloride that can be used for preparing sertraline hydrochloride, thus solving the aforementioned prior art problems since it does not require expensive toxic gas handling facilities, and it can be worked under mild and anhydrous conditions and with remarkably high yields.

According to the method of the invention, said amine hydrochloride can be used as such or dissolved in a suitable solvent to provide a solution, and is preferably selected among those having a low molecular weight.

Suitable amine hydrochlorides for the purposes of the invention are: ammonium chloride; primary alkylamine hydrochlorides, preferably wherein alkyl is C1–C6, for example methylamine hydrochloride or ethylamine hydrochloride; primary aralkylamine, for example aryl-C1–C4 alkyl such as benzylamine hydrochloride; secondary alkylamine, preferably di-C1–C4 alkyl, for example dimethylamine hydrochloride or diethylamine hydrochloride; tertiary alkylamine, for example triethylamine hydrochloride; aromatic amine hydrochloride, for example aniline hydrochloride; or heteroaromatic hydrochlorides, for example pyridine hydrochloride or 2,3,5-collidine hydrochloride.

In one embodiment, the present invention provides for a method of preparing sertraline hydrochloride polymorphs, in particular form I, II and V, from sertraline base comprising the following steps:

a) An amine hydrochloride is dissolved or suspended in a suitable solvent.
b) A solution of sertraline base in said solvent is mixed therewith.
c) The resulting mixture is kept at room temperature, or heated to a maximum temperature corresponding to the reflux temperature of said solvent, and maintained at said temperature for a period of time sufficient to cause precipitation of a crystalline form of sertraline hydrochloride.
d) Said mixture, if previously heated, is cooled to room temperature
e) Sertraline hydrochloride thus formed is separated by filtration.

In another embodiment, the present invention provides for a method of preparing sertraline hydrochloride polymorphs, in particular form I, II and V, from sertraline base comprising the following steps:

a) A solution of sertraline base is prepared by dissolving it in a suitable solvent b) An amine hydrochloride is added to said solution
c) The resulting mixture is kept at room temperature, or heated to a maximum temperature corresponding to the reflux temperature of the said solvent, and maintained at said temperature for a period of time sufficient to cause precipitation of a crystalline form of sertraline hydrochloride.
d) Said mixture, if previously heated, is cooled to room temperature
e) Sertraline hydrochloride thus formed is separated by filtration.

In one embodiment of the invention, in said step c) the solution is heated at a specific temperature selected in the range between room temperature and the solvent reflux temperature.

In another embodiment of the invention, in said step c) the solution is heated to the solvent reflux temperature.

For the purposes of the invention, said amine hydrochloride can be used as a commercially available product or may be prepared in situ, for example by reacting the corresponding amine with hydrogen chloride gas in a solvent.

In a preferred embodiment, a highly volatile amine salt is used such as methylamine hydrochloride, since purging the reaction mixture with an inert gas would cause the free amine to be removed.

Optionally, the crystallization step can be carried out by also adding seed crystal of the desired polymorph of sertraline hydrochloride to be obtained.

The separation step of Sertraline hydrochloride according to the method of the invention is preferably carried out by crystallization and may include, if required, a conjugate amine removal step, for example by purging, filtering, or washing and drying.

As regards said solvent for sertaline base and/or amine hydrochloride, it is chosen among the following in case the sertraline hydrochloride is separated as a selected crystalline form II: n-propanol, n-pentanol, n-hexanol, n-heptanol, n-octanol, acetonitrile, 1-methyl-2-piperidone, and mixtures thereof.

In case sertraline hydrochloride is separated as a selected crystalline form I, said solvent is preferably selected among the following: ethanol, propan-2-ol, ethyl acetate as such or optionally mixed with water.

In case sertraline hydrochloride is separated as a selected crystalline form V, said solvent is preferably selected among the following solvents mixed with water: ethanol, propan-2-ol.

Preferably, an anhydrous solvent is used in order to improve yields.

The starting sertraline base may be prepared by hydrolysis of sertraline mandelate with sodium hydroxide in toluene, followed by water work up and phase separation. The solvent of the resulting solution may be removed completely by distillation and subsequently said suitable solvent used to dissolve sertaline base is added. Suitable salts of sertraline to be used as starting materials include mandelate, citrate and acetate salts.

EXAMPLES

In order to further illustrate the present invention, examples are described in the following without limiting the scope of the invention.

It is made clear that Example A relates to a prior art preparation of sertraline base from sertraline mandelate. Sertraline mandelate mentioned in example A can be prepared, for instance, according to U.S. Pat. No. 5,248,699.

Example A 150 g of sertraline mandelate, 900 ml of water, 66 ml of 30% sodium hydroxide and 450 ml of toluene are fed into a 3-neck 2 litre flask equipped with mechanical stirrer, thermometer and dropping funnel.

The mixture is heated to 70° C. and maintained for 30 minutes under stirring until two clear emulsion-free phases are obtained.

The phases are decanted and separated. The aqueous phase is extracted with 300 ml toluene and the pooled organic phases are washed with 2×300 ml of demineralised water.

The organic phase is concentrated under vacuum to obtain sertraline base as an oil (103 g).

Example 1

A solution of 50 g of sertraline base in 200 ml of n-propanol is treated with one equivalent of pyridine hydrochloride at 50° C., under a nitrogen atmosphere, for about half an hour. The mixture is allowed to reach room temperature. At about 45° C. a gel begins to precipitate which fluidifies rapidly and transforms into a crystalline solid. Agitation is maintained for 1 hour at room temperature. The solid is filtered, washed and dried under vacuum. 52 g of sertraline hydrochloride form II (yield 93%) are obtained.

Example 2

A solution of 51.6 g of sertraline base in 310 ml of acetonitrile is treated with one equivalent of pyridine hydrochloride at room temperature, under nitrogen.

A crystalline solid begins to precipitate immediately and the temperature rises to 30° C. Agitation is maintained for 1 hour. The solid is isolated by filtration, washed and dried under vacuum. 52.5 g of sertraline hydrochloride form II (yield 91%) are obtained.

Example 3

A solution of 50 g of sertraline base in 200 ml of n-propanol is treated with one equivalent of triethylamine hydrochloride at 50° C., under nitrogen, for about half an hour. The mixture is allowed to reach room temperature and 0.5 g of sertraline hydrochloride form II acting as seed crystal are added. Agitation is maintained for 16 hours.

A crystalline solid slowly begins to precipitate, is filtered off, washed and dried under vacuum. 49 g of sertraline hydrochloride form II (yield 88%) are obtained.

Example 4

8.75 g of ammonium chloride are dissolved in 100 ml of n-propanol and 35 ml of water at T=50° C. 50 g of free sertraline base dissolved in 100 ml of n-propanol are added dropwise to the solution thus obtained. It Is heated under reflux and is maintained under agitation under a light nitrogen flow until ammonia is no longer evolved and the pH of the solution becomes slightly acidic. It is cooled to room temperature and is seed crystallized with 0.5 g of sertraline hydrochloride form II. A crystalline solid begins to precipitate and agitation is maintained for 1.5 hours. The solid is filtered, washed and dried under vacuum. 49.3 g of sertraline hydrochloride form II (yield 88%) are obtained.

Example 5

A solution of sertraline base (50 g) in ethanol (200 ml) was treated with one equivalent of pyridine hydrochloride at room temperature under nitrogen. The resulting solution was stirred at room temperature for 2 hours whereupon crystallisation occurred.

The solid was collected by filtration, washed with ethanol, and dried under vacuum. 52 g of sertraline hydrochloride form I (yield 93%) were obtained.

Example 6

A solution of sertraline base (52,8 g) in propan-2-ol (200 ml) was treated with one equivalent of pyridine hydrochloride at room temperature under nitrogen. The resulting solution was stirred rapidly at room temperature whereupon crystallisation occurred. After 2 hours stirring was stopped and the suspension filtered and washed with propan-2-ol.

The solid product was dried under vacuum. 53,7 g of sertraline hydrochloride form I (yield 91%) were obtained.

Example 7

In a solution of sertraline base (50 g) in ethyl acetate/water 10/1 (400 ml), ammonium chloride (8,7 g) was added. The resulting mixture was heated at reflux temperature and stirred for 15 hours during which ammonia evolution was observed and a white crystalline solid precipitated. When the evolution of ammonia ended the solid product was filtered, washed with ethyl acetate and dried under vacuum. 50,5 g of sertraline hydrochloride form I (yield 90%) were obtained.

Example 8

A solution of sertraline base (51,7 g) in etanol (200 ml) was diluted with water (50 ml) and pyridine hydrochloride (19,5) was added at room temperature under nitrogen. The reaction mixture was stirred at room temperature for 1 hour and the solid that crystallised was isolated by filtration, washed with etanol and dried under vacuum. 50 g of sertraline hydrochloride form V (yield 87%) were obtained.

Example 9

A solution of sertraline base (50 g) in propan-2-ol (200 ml) was diluted with water (50 ml) and pyridine hydrochloride (18,9 g) was added at room temperature under nitrogen. The reaction mixture was stirred at room temperature for 1 hour and the solid that crystallised was isolated by filtration, washed with propan-2-ol and dried under vacuum. 49,2 g of sertraline hydrochloride form V (yield 88%) were obtained.

The above detailed description of the invention shows that the purpose as set forth above of providing a convenient method of obtaining sertraline hydrochloride is successfully achieved, with remarkably high yields.

We claim:

1. A method for preparing sertraline hydrochloride polymorphs form I, II or V, characterized in that a solution of sertraline base or a salt thereof in a suitable solvent is reacted with an amine hydrochloride, so that sertraline hydrochloride precipitates in a crystallized form.

2. A method for preparing sertraline hydrochloride polymorphs according to claim 1 wherein sertraline hydrochloride is separated as a selected crystalline form I, II or V according to the selection of the said solvent.

3. A method according to claim 1 further comprising the following steps:
   a) dissolving or suspending an amine hydrochloride is in a suitable solvent;
   b) mixing a solution of sertraline base in the solvent is of step (a);
   c) maintaining the resulting mixture of step (b) at room temperature, or heating the resulting mixture of step (b) to a maximum temperature corresponding to the reflux temperature of the solvent, and maintaining the mixture at said temperature for a period of time sufficient to cause precipitation of a crystalline form of sertraline hydrochloride;
   d) cooling the mixture of step (c) to room temperature, if previously heated; and
   e) separating sertraline hydrochloride thus formed by filtration.

4. A method according to claim 1 further comprising the following steps:
   a) dissolving a solution of sertraline base in a suitable solvent;
   b) adding an amine hydrochloride to said solution;
   c) maintaining the resulting mixture of step (b) at room temperature, or heating the resulting mixture of step (b) to a maximum temperature corresponding to the reflux temperature of the solvent, and maintaining the mixture at said temperature for a period of time sufficient to cause precipitation of a crystalline form of sertraline hydrochloride;
   d) cooling said mixture to room temperature, if previously heated;
   e) separating sertraline hydrochloride thus formed by filtration.

5. The method according to claim 1, characterized in that said amine hydrochloride is selected from the group consisting of:
   ammonium chloride;
   primary alkylamine hydrochlorides;
   primary aralkylamine hydrochlorides;
   secondary alkylamine hydrochlorides;
   tertiary alkylamine hydrochlorides;
   aromatic amine hydrochlorides;
   and heteroaromatic hydrochlorides.

6. A method according to claim 5, characterized in that said amine hydrochloride is a primary alkylamine hydrochloride wherein alkyl is C1–C6.

7. A method according to claim 5, characterized in that said amine hydrochloride is a primary aralkylamine hydrochloride including aryl-C1–C4 alkyl.

8. A method according to claim 5, characterized in that said amine hydrochloride is a secondary alkylamine including di-C1–C4 alkyl.

9. A method according to claim 5, characterized in that said amine hydrochloride is a tertiary alkylamine.

10. A method according to claim 5, characterized in that said amine hydrochloride is an aromatic amine hydrochloride or an heteroaromatic hydrochloride.

11. A method according to claim 2 characterized in that, in case sertraline hydrochloride is to be separated as a selected crystalline form II, said solvent is selected from the group consisting of: n-propanol, n-pentanol, n-hexanol, n-heptanol, n-octanol, acetonitrile, 1-methyl-2-piperidone, and mixtures thereof.

12. A method according to claim 2 characterized in that, in case sertraline hydrochloride is separated as a selected crystalline form I, said solvent is selected from the group consisting of ethanol, propan-2-ol, ethyl acetate and aqueous solutions thereof.

13. A method according to claim 2 characterized in that, in case sertraline hydrochloride is separated as a selected crystalline form V, said solvent is selected from the group consisting of the following solvents mixed with water: ethanol, propan-2-ol.

14. The method according to claim 6, wherein said amine hydrochloride is selected from the group consisting of methylamine hydrochloride and ethylamine hydrochloride.

15. The method according to claim 7, wherein said amine hydrochloride is benzylamine hydrochloride.

16. The method according to claim 8, wherein the amine hydrochloride is selected from the group consisting of dimethylamine and diethylamine hydrochloride.

17. The method according to claim 9, wherein the amine hydrochloride is triethylamine hydrochloride.

18. The method according to claim 10, wherein the amine hydrochloride is selected from the group consisting of aniline hydrochloride, pyridine hydrochloride and 2,3,5-collidine hydrochloride.

* * * * *